United States Patent [19]

Schmitt et al.

[11] Patent Number: 5,122,435
[45] Date of Patent: Jun. 16, 1992

[54] AMIDO-CONTAINING AZULENE SQUARIC ACID DYES, INTERMEDIATES THEREFOR AND OPTICAL RECORDING MEDIUM

[75] Inventors: Michael Schmitt, Weinheim; Bernhard Albert, Maxdorf; Sibylle Brosius; Klaus D. Schomann, both of Ludwigshafen; Harald Kuppelmaier, Goennheim, all of Fed. Rep. of Germany

[73] Assignee: BASF Aktiengesellschaft, Ludwigshafen, Fed. Rep. of Germany

[21] Appl. No.: 600,811

[22] Filed: Oct. 22, 1990

[30] Foreign Application Priority Data

Oct. 25, 1989 [DE] Fed. Rep. of Germany ....... 3935526

[51] Int. Cl.⁵ ................... G03C 1/492; C07D 305/00; C07C 211/00
[52] U.S. Cl. ................... 430/270; 430/495; 430/945; 546/189; 558/303; 558/426; 558/428; 558/433; 560/36; 560/42; 564/152; 564/158; 564/307; 549/510; 549/511
[58] Field of Search ........... 549/511, 510; 546/169; 564/152, 156, 307; 560/36, 42; 558/428, 426, 433, 303; 430/495, 945, 270

[56] References Cited

FOREIGN PATENT DOCUMENTS 0310080 4/1989 European Pat. Off. .
0341541 11/1989 European Pat. Off. .
3505750 8/1986 Fed. Rep. of Germany .
3505751 8/1986 Fed. Rep. of Germany .

OTHER PUBLICATIONS

Abstract, *Dyes and Their Intermediates*, 1968, p. 8.
Angewandte Chemie, 78, 1966, p. 937, W. Ziegenbein, et al., "Kondensationsprodukte Aus Quadratsaure und Azulen-Kohlenwasser-Stoffen".
Dyes and Pigments, vol. 8, 1987, pp. 381–388, S. H. Kim et al., "Synthesis and Characteristics of Infrared Absorbing 2:1 Nickel Complex Dyes".

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

Amido-containing azulene-aquaric acid dyes of the formula

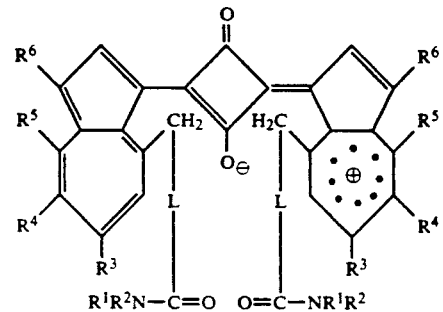

where

L is $C_1$–$C_{12}$-alkylene which may be substituted by phenyl, $R^1$ and $R^2$ are each independently of the other hydrogen, substituted or unsubstituted $C_1$–$C_{20}$-alkyl, $C_5$–$C_7$-cycloalkyl, substituted or unsubstituted phenyl, 2,2,6,6-tetramethylpiperidin-4-yl or cyclohexylaminocarbonyl and $R^3$, $R^4$, $R^5$ and $R^6$ are each independently of the others hydrogen or substituted or unsubstituted $C_1$–$C_{12}$-alkyl, with the proviso that when $R^6$ is hydrogen the positions of the substituents $CH_2$—L—CO—$NR^1R^2$ and $R^5$ on either or both azulene rings may also be interchanged with each other within an azulene ring are used in an optical recording medium.

8 Claims, No Drawings

AMIDO-CONTAINING AZULENE SQUARIC ACID DYES, INTERMEDIATES THEREFOR AND OPTICAL RECORDING MEDIUM

The present invention relates to novel amido-containing azulenesquaric acid dyes of the formula I

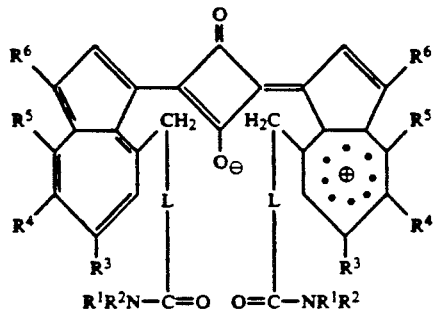

where

L is $C_1$–$C_{12}$-alkylene which may be substituted by phenyl, $R^1$ and $R^2$ are identical or different and each is independently of the other hydrogen, substituted or unsubstituted $C_1$–$C_{20}$-alkyl, $C_5$–$C_7$-cycloalkyl, substituted or unsubstituted phenyl, 2,2,6,6-tetramethylpiperidin-4-yl or cyclohexylaminocarbonyl and $R^3$, $R^4$, $R^5$ and $R^6$ are identical or different and each is independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or by cyano, with the proviso that when $R^6$ is hydrogen the positions of the substituents $CH_2$—L—CO—$NR^1R^2$ and $R^5$ on either or both azulene rings may also be interchanged with each other within an azulene ring; to intermediates therefor; and to an optical recording medium which contains the novel dyes.

The cost-efficient manufacture of optical data recording media requires dyes having particular properties. These dyes should be strongly absorbing within the range from 700 to 900 nm to provide layers that may be writable with semiconductor lasers, in layer form be highly reflective in the near infrared (700–900 nm) to make possible a simple layer construction (without reflector layer), be highly soluble for example in order that the thin storage layer may be applied to a base material by spincoating, and be highly stable in thin layers.

The prior art storage materials frequently are defective on at least one count.

It is an object of the present invention to provide novel dyes which are free or substantially free of the abovementioned defects.

We have found that this object is achieved by the amido-containing azulenesquaric acid dyes of the formula I defined at the beginning.

Any alkylene and alkyl appearing in the abovementioned formula I may be either straight-chain or branched.

In any substituted alkyl appearing in the formula I the substituents may be for example $C_1$–$C_4$-alkoxy, phenyl, $C_1$–$C_4$-alkylphenyl, $C_1$–$C_4$-alkoxyphenyl, 2,2,6,6-tetramethylpiperidin-4-ylaminocarbonyl and 1-acetyl-2,2,6,6-tetramethylpiperidin-4-ylaminocarbonyl.

In any substituted phenyl appearing in the formula I suitable substituents are for example $C_1$–$C_4$-alkyl, $C_1$–$C_4$-alkoxy and halogen (preferably fluorine, chlorine or bromine).

L is for example methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene, dodecamethylene, phenylethylene or 1-phenyl-1,3-propylene.

$R^1$, $R^2$, $R^3$, $R^4$, $R^5$ and $R^6$ in the formula I are each for example methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, nonyl, decyl, undecyl or dodecyl.

$R^1$ and $R^2$ may each also be tridecyl, tetradecyl, pentadecyl, hexadecyl, heptadecyl, octadecyl, nonadecyl, icosyl, cyclopentyl, cyclohexyl, cycloheptyl, phenyl, 2- or 4-methylphenyl, 2- or 4-methoxyphenyl, 2- or 4-chlorophenyl or 2,4-dichlorophenyl.

$R^3$, $R^4$, $R^5$ and $R^6$ may each also be for example fluoromethyl, chloromethyl, difluoromethyl, trifluoromethyl, trichloromethyl, 2-fluoroethyl, 2-chloroethyl, 2-bromoethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 2-isopropoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl)ethyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

Preference is given to the azulenesquaric acid dyes of the formula I where $R^3$, $R^4$, $R^5$ and $R^6$ are each $C_1$–$C_6$-alkyl or hydrogen.

Particular preference is given to azulenesquaric acid dyes of the formula I in which $R^3$ and $R^5$ are each methyl, $R^4$ and $R^6$ are each hydrogen, and L, $R^1$ and $R^2$ are each as defined above. These dyes conform to the formula Ia

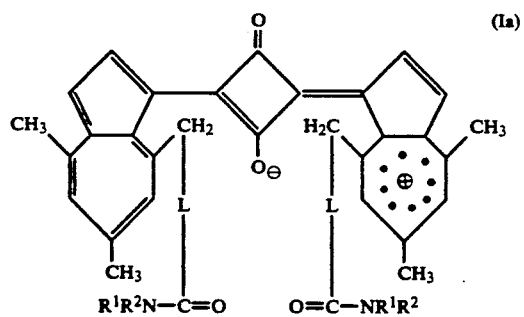

Very particular preference is given to azulenesquaric acid dyes of the formula I where $R^3$ and $R^5$ are each hydrogen, $R^4$ is isopropyl, $R^6$ is methyl, and L, $R^1$ and $R^2$ are each as defined above. These dyes conform to the formula Ib

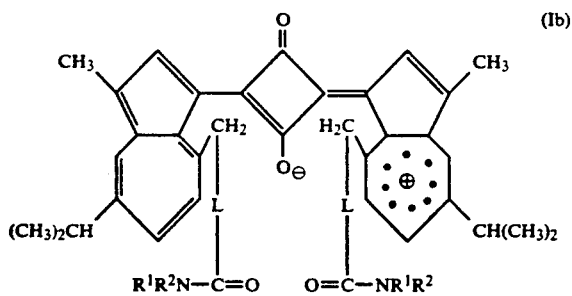

Preference is further given to azulenesquaric acid dyes of the formula I where $R^1$ and $R^2$ are each independently of the other hydrogen or $C_1$-$C_{20}$-alkyl which may be substituted by phenyl.

The novel dyes of the formula I are obtained from azulene derivatives of the formula II where L, $R^1$, $R^2$, $R^3$, $R^4$, $R^5$ and $R^6$ are each as defined above by reaction with squaric acid of the formula III according to the following equation:

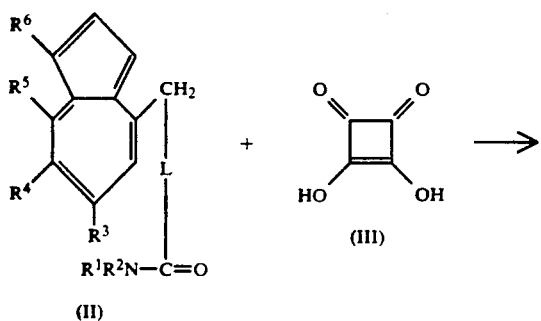

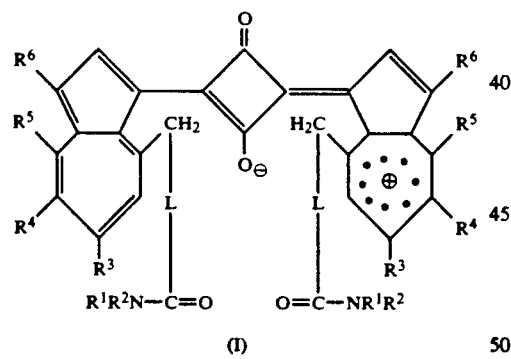

In those azulene derivatives of the formula II where $R^6$ is hydrogen, the bond to the squaric acid can form at different positions on the five-membered ring, which may produce isomeric products in which the ring positions of substituents $CH_2$—L—CO—$NR^1R^2$ and $R^5$ are interchanged with each other, as mentioned above. This is because it is then necessary to distinguish those compounds where the bond to the squaric acid forms on that side where the substituent $CH_2$—L—CO—$NR^1R^2$ is attached from those in which the bond to the squaric acid forms at that side where the substituent $R^6$ is attached. These isomeric compounds can be separated by chromatography. For use in storage layers, however, it is customary to use the isomeric mixtures.

The method of preparation is known per se and is described for example in Angew. Chem. 78 (1966) 937, and in EP-A-310,080.

The present invention further provides novel amido-containing azulenes of the formula II

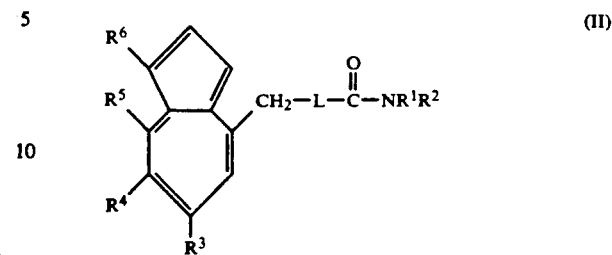

where

L is $C_1$-$C_{12}$-alkylene which may be substituted by phenyl, $R^1$ and $R^2$ are identical or different and each is independently of the other hydrogen, substituted or unsubstituted $C_1$-$C_{20}$-alkyl, $C_5$-$C_7$-cycloalkyl, substituted or unsubstituted phenyl, 2,2,6,6-tetramethylpiperidin-4-yl or cyclohexylaminocarbonyl and $R^3$, $R^4$, $R^5$ and $R^6$ are identical or different and each is independently of the others hydrogen or $C_1$-$C_{12}$-alkyl which may be substituted by halogen, $C_1$-$C_{12}$-alkoxy, phenyl, substituted phenyl, $C_1$-$C_{12}$-alkoxycarbonyl or by cyano.

Concerning examples of L, $R^1$, $R^2$, $R^3$, $R^4$, $R^5$ and $R^6$, reference is made to the previous illustration.

The amido-containing azulene derivatives of the formula II are obtained for example by starting from the corresponding free azulenealkylcarboxylic acids of the formula IV

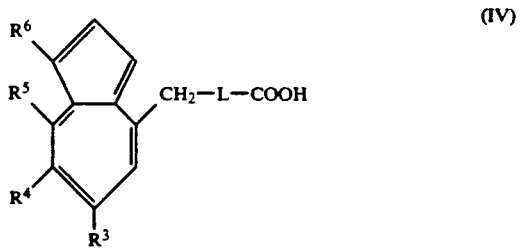

where $R^3$, $R^4$, $R^5$ and $R^6$ are each as defined above. The preparation of these products is described for example in EP-A-310,080.

For instance, those azulene derivatives of the formula IVa or IVb

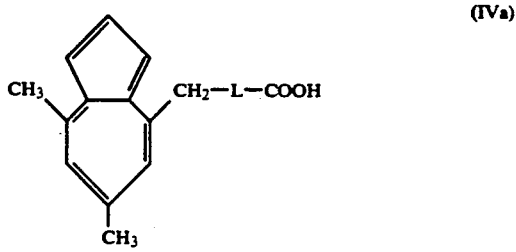

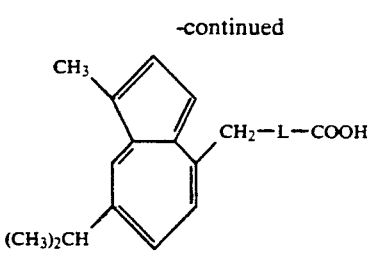

where L is in each case as defined above, are particularly highly suitable for conversion.

The reactants for the azulenealkylcarboxylic acids IV are organic primary or secondary amines of the formula V $$R^1R^2NH \qquad (IV)$$

where $R^1$ and $R^2$ are each as defined above.

The reaction of the azulenealkylcarboxylic acids IV with the amines V is carried out in a conventional manner. To this end, the azulenealkylcarboxylic acid can be reacted with the amine for example in an inert organic solvent (e.g. dichloromethane, 1,1,2-trichloroethane, toluene, naphtha or cyclohexane) using a condensing agent (e.g. dicyclohexylcarbodiimide) at from 10° to 60° C. in the presence or absence of a catalyst (for example a tertiary amine). In general, the amine V is used in excess in this reaction.

It is a further object of the present invention to provide a novel optical recording medium containing azulenesquaric acid derivatives as storage materials which is simple to manufacture, which is easy to write to and subsequently also to read back from, for which the signal-to-noise ratio should be very high, and which exhibits high storage layer stability.

We have found that this further object is achieved by an optical recording medium comprising a base material and a radiation-sensitive thin coating film which contains a dye with or without a binder, wherein the dye has the formula I

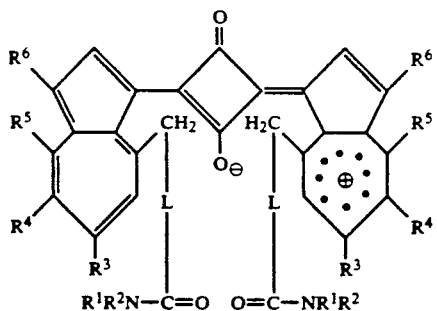

where
L is $C_1$–$C_{12}$-alkylene which may be substituted by phenyl,
$R^1$ and $R^2$ are identical or different and each is independently of the other hydrogen, substituted or unsubstituted $C_1$–$C_{20}$-alkyl, $C_5$–$C_7$-cycloalkyl, substituted or unsubstituted phenyl, 2,2,6,6-tetramethylpiperidin-4-yl or cyclohexylaminocarbonyl and
$R^3$, $R^4$, $R^5$ and $R^6$ are identical or different and each is independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or by cyano,
with the proviso that when $R^6$ is hydrogen the positions of the substituents $CH_2$—L—CO—$NR^1R^2$ and $R^5$ on either or both azulene rings may also be interchanged with each other within an azulene ring.

Preference is given to an optical recording medium which contains azulenesquaric acid dyes of the formula I where $R^3$, $R^4$, $R^5$ and $R^6$ are each $C_1$–$C_6$-alkyl or hydrogen.

Particular preference is given to an optical recording medium which contains azulenesquaric acid dyes of the formula I where $R^3$ and $R^5$ are each methyl and $R^4$ and $R^6$ are each hydrogen.

Very particular preference is given to an optical recording medium which contains azulenesquaric acid dyes of the formula I where $R^3$ and $R^5$ are each hydrogen, $R^4$ is isopropyl and $R^6$ is methyl.

Preference is further given to an optical recording medium which contains azulenesquaric acid dyes of the formula I where $R^1$ and $R^2$ are each independently of the other hydrogen or $C_1$–$C_{20}$-alkyl which may be substituted by phenyl.

Suitable base materials are conveniently transparent base materials such as glass or plastics. Suitable plastics are for example poly(meth)acrylates, polycarbonates, polyesters, epoxys, polyolefins (e.g. polymethylpentene), polyamide, polyvinyl chloride, polystyrene and polyvinyl esters.

A particularly preferred recording medium is based on a support of polycarbonate or poly(meth)acrylate, in particular polycarbonate.

Preference is further given to an optical recording medium which contains from 1 to 30% by weight, based on dye, of binder.

The novel azulenesquaric acid dyes of the formula I have good optical characteristics. In addition, the novel compounds have been observed to give very stable pure dye layers. This is because no recrystallization of the pure dye layer was observed and it is thus possible to dispense with the addition of polymeric binders. Moreover, the lightfastness (stability) is significantly higher than that of existing methine dyes, so that the addition of stabilizers to the layer formulation can be limited to a minimum. Another particular advantage is the ready solubility of the novel dyes I in most organic solvents, so that these dyes can be applied directly (without protective layer) to structured plastics substrates, in particular polycarbonate substrates, by spincoating.

As mentioned above, the spincoating solution preferably contains a binder to ensure good long term stability and in particular to optimize its viscosity. Preferably the solution contains from 1 to 30% by weight, based on the amount of dissolved solids in the solution, of a binder.

Suitable binders are for example polyorganosiloxanes, epoxys, poly(meth)acrylates, polystyrene homopolymers and copolymers, polyvinylcarbazole, polyvinylpyrrolidone, polyimidazole copolymers, polyvinyl ester copolymers, polyvinyl ether copolymers, polyvinylidene chloride polymers, acrylonitrile copolymers, polyvinyl chloride or copolymers thereof, cellulose acetate and nitrocellulose.

A preferred recording medium contains a binder based on a vinylpyrrolidone/vinyl acetate copolymer or a polyvinyl chloride/polyvinyl ether copolymer.

The optical recording medium according to the present invention is advantageously prepared by spincoating with a solution containing an organic solvent and an azulenesquaric acid dye I, with or without a binder. Advantageously, the level of dissolved solids in the spincoating solution is from 1 to 30% by weight, based on the solution.

Suitable solvents are for example propanol, isopropanol, butanol, diacetone alcohol, methyl ethyl ketone, toluene, bromoform, 1,1,2-trichloroethane and mixtures thereof.

Optionally, the solution may also contain up to 10% by weight, based on the level of dissolved solids in the spincoating solution, of additives, for example antioxidants, singlet oxygen quenchers or UV absorbers.

Preferably, the spincoating solution contains up to 5% by weight, based on the level of dissolved solids in the spincoating solution, of a mixture of a plurality of antioxidants, singlet oxygen quenchers and UV absorbers. On using antioxidants which likewise absorb, in the near infrared, for example nickel thiolene complexes, as described for example in DE-A-3,505,750, DE-A-3,505,751 or Dyes and Pigments 8 (1987), 381-88, it is preferable for up to 10% by weight, based on the level of dissolved solids in the spincoating solution, to be present in the solution.

Spincoating is for the purposes of the present invention the application of the solution to a rotating base material, which advantageously has a round shape. However, it is also possible to apply the solution to a base which is initially at rest and then set in rotation. The solution is conveniently applied to the base by means of a syringe or capillary or by means of a mechanical pump.

The base generally rotates at a speed of from 5 to 7000 rpm, preferably from 500 to 5000 rpm, the solution being advantageously applied at a relatively low speed (about 500–2000 rpm) and then dried at a higher speed (about 5000–7000 rpm). The thickness of the layer which is sensitive to laser light is from 40 to 160 nm, preferably from 80 to 120 nm. The thickness is dependent on the speed of rotation, the concentration and viscosity of the spincoating solution and the temperature.

In the optical recording medium according to the present invention, the layer which is sensitive to laser light is present in the form of a homogeneous, thin, smooth layer of high optical quality. For instance, the reflectivities are in general within a range greater than 12%.

The novel recording medium is also sufficiently sensitive to the wavelength of the laser light source used; that is, the incidence of light pulses having an energy content of a few nJ which are focused to a focal spot diameter of $\leq 1$ μm leads to the formation of pits with an excellent signal-to-noise ratio.

Particularly suitable laser light sources on account of the small size of the device, its low energy consumption and the possibility of direct modulation of the optical output through modulation of the electrical drive current are solid state injection lasers which emit in the near infrared, in particular the AlGaAs laser which emits within the wavelength range from about 750 to 900 nm.

The Examples which follow further illustrate the invention.

EXAMPLE 1

Preparation of N-butyl-3-(7-isopropyl-1-mathylazulen-4-yl)propionamide 4.9 g (0.024 mol) of dicyclohexylcarbodiimide in 10 ml of dichloromethane were added dropwise at 0° C. to a solution of 5.1 g (0.02 mol) of (7-isopropyl-1-methylazulen-4-yl) propionic acid in 50 ml of dichloromethane, and the mixture was stirred for 30 minutes. 3.7 g (0.05 mol) of n-butylamine were then added, and stirring was continued at room temperature for 2 hours. The precipitate (dicyclohexylurea) was filtered off. The filtrate was repeatedly washed with 2N hydrochloric acid and dried over sodium sulfate, and thereafter the solvent was evaporated off. The residue was chromatographed over silica gel (9:1 v/v ethyl acetate:petroleum ether). This gave 2.9 g (47%) of the target product as a highly viscous blue oil.

Physical data: IR (KBr): 3304 (N—H); 2954, 2931, 2852, (C—H); 1643, 1627 (C=O); 1556, 1464, 1435, 1387 cm$^{-1}$. $^1$H—NMR (CDCl$_3$): δ=0.95 (t, 3H); 1.22 (m, 6H); 1.35 (d, 6H); 2.65 (s, 3H); 3.05 (m, 1H); 3.15 (m, 2H); 3.48 (t, 2H); 5.50 (bs, 1H); 7.00 (d, 1H); 7.29 (2, 1H); 7.38 (d, 1H); 7.60 (d, 1H); 8.18 (s, 1H) ppm. $^{13}$C—NMR (CDCl$_3$): δ=12.83; 13.65; 20.02; 24.69 (2C); 31.68; 34.00; 38.00; 38.27; 39.35; 112.26; 124.50; 125.46; 133.29; 135.18; 136.49; 136.69; 136.99; 140.24; 147.21; 172.03 ppm. MS: e/m=311 (35%, M+).

The method of Example 1 was also used to prepare the azulene derivatives listed in Table 1.

All the structures are confirmed by IR, $^1$H—NMR, $^{13}$C—NMR and MS spectra.

TABLE 1

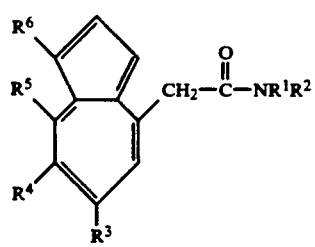

| Example No. | L—C(O)NR$^1$R$^2$ | R$^3$ | R$^4$ | R$^5$ | R$^6$ | MS[M$^\oplus$] | IR($\tilde{\nu}$/cm$^{-1}$) [NH; C=O] |
|---|---|---|---|---|---|---|---|
| 2 | 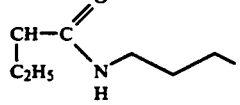 | H | CH(CH$_3$)$_2$ | H | CH$_3$ | 339.5 | 3294; 1645 |

TABLE 1-continued $$\text{structure with } R^6, R^5, R^4, R^3 \text{ on azulene-like ring with } CH_2-C(=O)-NR^1R^2$$

| Example No. | L—C(O)NR¹R² | R³ | R⁴ | R⁵ | R⁶ | MS[M⊕] | IR(ν̃/cm⁻¹) [NH; C=O] |
|---|---|---|---|---|---|---|---|
| 3 | CH₂—C(=O)—NH—t-Bu | H | CH(CH₃)₂ | H | CH₃ | 311.5 | 3280; 1640 |
| 4 | CH(C₂H₅)—C(=O)—NH—t-Bu | H | CH(CH₃)₂ | H | CH₃ | 339.5 | 3312; 1639 |
| 5 | CH₂—C(=O)—NH—cyclohexyl | H | CH(CH₃)₂ | H | CH₃ | 337.5 | 3301; 1642 |
| 6 | CH(C₂H₅)—C(=O)—NH—cyclohexyl | H | CH(CH₃)₂ | H | CH₃ | 365.5 | 3312; 1636 |
| 7 | CH₂—C(=O)—NH—n-hexyl | H | CH(CH₃)₂ | H | CH₃ | 339.5 | 3291; 1643 |
| 8 | CH(C₂H₅)—C(=O)—NH—n-hexyl | H | CH(CH₃)₂ | H | CH₃ | 367.5 | 3294; 1644 |
| 9 | CH₂—C(=O)—NH—CH(CH₃)CH₂CH₂CH₂CH(CH₃)₂ | H | CH(CH₃)₂ | H | CH₃ | 367.5 | 3289; 1640 |
| 10 | CH(C₂H₅)—C(=O)—NH—CH(CH₃)CH₂CH₂CH₂CH(CH₃)₂ | H | CH(CH₃)₂ | H | CH₃ | 395.6 | 3291; 1637 |
| 11 | CH₂—C(=O)—NH—phenyl | H | CH(CH₃)₂ | H | CH₃ | 331.5 | 3313; 1663 |

TABLE 1-continued

[Structure: Azulene core with R⁶, R⁵, R⁴, R³ substituents and CH₂-C(=O)-NR¹R² side chain]

| Example No. | L—C(O)NR¹R² | R³ | R⁴ | R⁵ | R⁶ | MS[M⊕] | IR($\tilde{\nu}$/cm⁻¹) [NH; C=O] |
|---|---|---|---|---|---|---|---|
| 12 | CH(C₂H₅)—C(O)—NH—C₆H₅ | H | CH(CH₃)₂ | H | CH₃ | 359.5 | 3300; 1657 |
| 13 | CH₂—C(O)—NH—CH₂-t-Bu | H | CH(CH₃)₂ | H | CH₃ | 325.5 | 3321; 1637 |
| 14 | CH(C₂H₅)—C(O)—NH—CH₂-t-Bu | H | CH(CH₃)₂ | H | CH₃ | 353.5 | 3306; 1657 |
| 15 | CH₂—C(O)—NH—CH₂—C₆H₄—OCH₃ | H | CH(CH₃)₂ | H | CH₃ | 375.52 | 3301; 1639 |
| 16 | CH(C₂H₅)—C(O)—NH—CH₂—C₆H₄—OCH₃ | H | CH(CH₃)₂ | H | CH₃ | 403.5 | 3301; 1639 |
| 17 | CH₂—C(O)—NH—CH(CH₃)—CH₂—CH₂—C₆H₅ | H | CH(CH₃)₂ | H | CH₃ | 387.5 | 3319; 1638 |
| 18 | CH(C₂H₅)—C(O)—NH—CH(CH₃)—CH₂—CH₂—C₆H₅ | H | CH(CH₃)₂ | H | CH₃ | 415.5 | 3309; 1638 |
| 19 | CH₂—C(O)—N(CH₃)(n-butyl) | H | CH(CH₃)₂ | H | CH₃ | 325.5 | —; 1646 |

TABLE 1-continued

| Example No. | L—C(O)NR¹R² | R³ | R⁴ | R⁵ | R⁶ | MS[M⊕] | IR($\tilde{\nu}$/cm⁻¹) [NH; C=O] |
|---|---|---|---|---|---|---|---|
| 20 | CH(C₂H₅)—C(O)—N(CH₃)(n-butyl) | H | CH(CH₃)₂ | H | CH₃ | 353.5 | —; 1640 |
| 21 | CH₂—C(O)—N(CH₃)(cyclohexyl) | H | CH(CH₃)₂ | H | CH₃ | 351.5 | —; 1641 |
| 22 | CH(C₂H₅)—C(O)—N(CH₃)(cyclohexyl) | H | CH(CH₃)₂ | H | CH₃ | 379.5 | —; 1634 |
| 23 | CH₂—C(O)—N(CH₃)(phenyl) | H | CH(CH₃)₂ | H | CH₃ | 345.5 | —; 1658 |
| 24 | CH(C₂H₅)—C(O)—N(CH₃)(phenyl) | H | CH(CH₃)₂ | H | CH₃ | 373.5 | —; 1654 |
| 25 | CH₂—C(O)—NH—CH(CH₂C(CH₃)₃)(NH-t-Bu) | H | CH(CH₃)₂ | H | CH₃ | 394.61 | 3284; 1637 |
| 26 | CH(C₂H₅)—C(O)—NH—CH(CH₂C(CH₃)₃)(NH-t-Bu) | H | CH(CH₃)₂ | H | CH₃ | 442.6 | 3275; 1639 |
| 27 | CH₂—C(O)—N(cyclohexyl)—C(O)—NH—cyclohexyl | H | CH(CH₃)₂ | H | CH₃ | 462.6 | 3271; 1704; 1639 |

TABLE 1-continued

[Structure: Azulene core with R6, R5, R4, R3 substituents and CH2-C(=O)-NR1R2 group]

| Example No. | L—C(O)NR¹R² | R³ | R⁴ | R⁵ | R⁶ | MS[M⊕] | IR(ṽ/cm⁻¹) [NH; C=O] |
|---|---|---|---|---|---|---|---|
| 28 | [Structure: CH(C2H5)—C(=O)—N(cyclohexyl)—CH2—C(=O)—NH—cyclohexyl] | H | CH(CH₃)₂ | H | CH₃ | 490.7 | 3350; 3405; 1705; 1657 |
| 29 | [Structure: CH2—C(=O)—NH—CH(CH3)—CH(OMe)2] | H | CH(CH₃)₂ | H | CH₃ | 357.5 | 3309; 1642 |
| 30 | [Structure: CH(C2H5)—C(=O)—NH—CH(CH3)—CH(OMe)2] | H | CH(CH₃)₂ | H | CH₃ | 385.5 | 3305; 1639 |
| 31 | [Structure: CH2—CH2—C(=O)—NH—t-Bu] | H | CH(CH₃)₂ | H | CH₃ | 325.5 | 3290; 1637 |

EXAMPLE 32

Preparation of (7-isopropyl-1-methylazulen-4-yl)propionamide 100 ml of butyllithium solution (in hexane, 0.16 mol) were slowly added dropwise at −10° C. to a solution of 23.6 g (0.12 mol) of guajazulene and 26.4 ml (0.19 mol) of diisopropylamine in 400 ml of methyl t-butyl ether in the course of 1 hour, and the mixture was stirred at 0° C. for 1 hour. A suspension of 14.0 g (0.15 mol) of chloroacetamide was then added, and stirring was continued at room temperature for 12 hours. The reaction mixture was hydrolyzed with 200 ml of water. The organic phase was repeatedly washed with water and dried over sodium sulfate. After the solvent had been evaporated off under reduced pressure, the residue was chromatographed over silica gel. This gave 7.1 g (23%) of the amide as blue crystals of melting point 149°–152° C.

Physical data: IR (KBr): 3186 (N—H); 2961, (C—H); 1651 (C=O); 1456, 1433, 1403, 774 cm⁻¹. ¹H—NMR (CDCl₃): δ=1.35 (d, 6H); 2.65 (s, 3H); 2.70 (m, 2H); 3.08 (m, 1H); 3.30 (t, 2H); 5.50 (bs, 2H); 7.00 (d, 1H); 7.28 (d, 1H); 7.38 (d, 1H); 7.60 (d, 1H); 8.15 (s, 1H) ppm. ¹³C—NMR (CDCl₃): δ=12.82; 24.69 (2C); 33.62; 37.05; 38.28; 112.25; 124.37; 125.60; 133.37; 135.26; 136.61; 136.78; 136.99; 140.38; 146.93; 174.48 ppm. MS: e/m=255 (100%, M+).

EXAMPLE 33

Preparation of the bis[N-butyl-(7-isopropyl-1-methylazulen-4-yl)propionamide]squaric acid dye A mixture of 2.7 g (4 mmol) of N-(n-butyl)-3-(7-isopropyl-1-methylazulen-4-yl)propionamide, 1.0 g (8.7 mmol) of squaric acid, 40 ml of n-butanol and 40 ml of toluene was refluxed under a water separator for 3 hours. After the solvent had been distilled off, the residue was recrystallized from ethyl acetate/methanol. This gave 1.4 g (50%) of the dye as metallically bright crystals of melting point 122°–125° C.

Physical data: UV (CH₂Cl₂): λ$_{max}$(ε)=775 (119 000) nm. IR (KBr): 3300 (N—H); 2958, (C—H); 1643, 1643, 1612 (C=O); 1546, 1435, 1387, 1332, 1251, 1072, 1013 cm⁻¹. ¹H—NMR (CDCl₃): δ=0.85 (t, 6H); 1.05–1.45 (m, 8H); 1.35 (d, 12H); 2.55 (s, 6H); 2.73 (t, 4H); 3.10 (cm, 6H); 4.18 (t, 4H); 6.68 (bs, 2H); 7.65 (s, 4H); 8.10 (s, 2H); 8.95 (s, 2H) ppm. ¹³C—NMR (CDCl₃): δ=13.04 (2C); 13.64 (2C); 20.08 (2C); 24.19 (4C); 31.61 (2C); 35.55 (2C); 37.85 (2C); 38.35 (2C); 39.34 (2C); 121.22 (2C); 131.22 (2C); 134.26 (2C); 134.72 (2C); 138.49 (2C); 140.24 (2C); 141.80 (12C); 148.17 (2C); 151.09 (2C); 154.60 (2C); 171.99 (2C); 180.57 (2C); 183.68 (2C); ppm. MS: e/m=700 (15%, M+).

The method of Example 33 was also used to prepare the squaric acid dyes listed in Table 2, which were additionally characterized by IR, $^1$H—NMR, $^{13}$C—NMR and MS spectra.

TABLE 2

[Structure showing squaric acid dye with R³, R⁴, R⁵, R⁶ substituents on cyclopentene rings fused to the central squaric acid core, with CH₂—L—C(O)NR¹R² substituents]

| Example No. | L—C(O)NR¹R² | R³ | R⁴ | R⁵ | R⁶ | λmax (ε) [nm] | mp. [°C.] |
|---|---|---|---|---|---|---|---|
| 34 | CH(C₂H₅)—C(O)—NH—n-butyl | H | CH(CH₃)₂ | H | CH₃ | 774 (107 000) | 147–150 |
| 35 | CH₂—C(O)—NH—t-Bu | H | CH(CH₃)₂ | H | CH₃ | 776 (116 000) | 213–214 |
| 36 | CH(C₂H₅)—C(O)—NH—t-Bu | H | CH(CH₃)₂ | H | CH₃ | 775 (107 000) | 240–241 |
| 37 | CH₂—C(O)—NH—cyclohexyl | H | CH(CH₃)₂ | H | CH₃ | 778 (116 000) | 242–245 |
| 38 | CH(C₂H₅)—C(O)—NH—cyclohexyl | H | CH(CH₃)₂ | H | CH₃ | 774 (104 000) | 218–222 |
| 39 | CH₂—C(O)—NH—n-hexyl | H | CH(CH₃)₂ | H | CH₃ | 775 (116 000) | 234–237 |
| 40 | CH(C₂H₅)—C(O)—NH—n-hexyl | H | CH(CH₃)₂ | H | CH₃ | 774 (111 000) | 232–235 |
| 41 | CH₂—C(O)—NH—CH(CH₃)CH₂CH₂CH₂CH(CH₃)₂ | H | CH(CH₃)₂ | H | CH₃ | 770 (125 000) | 205–207 |
| 42 | CH(C₂H₅)—C(O)—NH—CH(CH₃)CH₂CH₂CH₂CH(CH₃)₂ | H | CH(CH₃)₂ | H | CH₃ | 768 (112 000) | 176–180 |

TABLE 2-continued
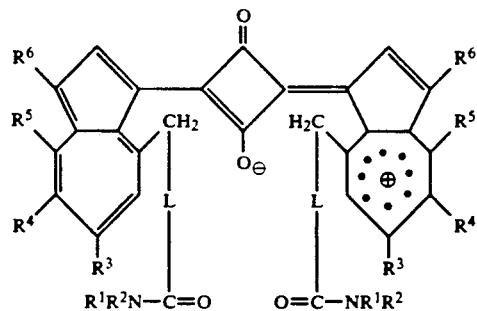
| Example No. | L—C(O)NR¹R² | R³ | R⁴ | R⁵ | R⁶ | λmax (ε) [nm] | mp. [°C.] |
|---|---|---|---|---|---|---|---|
| 43 | CH₂—C(O)—NH—C₆H₅ | H | CH(CH₃)₂ | H | CH₃ | 772 (141 000) | 263–264 |
| 44 | CH(C₂H₅)—C(O)—NH—C₆H₅ | H | CH(CH₃)₂ | H | CH₃ | 770 (127 000) | 247–248 |
| 45 | CH₂—C(O)—NH—CH₂-t-Bu | H | CH(CH₃)₂ | H | CH₃ | 771 (137 000) | 214–216 |
| 46 | CH(C₂H₅)—C(O)—NH—CH₂-t-Bu | H | CH(CH₃)₂ | H | CH₃ | 769 (121 000) | 229–230 |
| 47 | CH₂—C(O)—NH—CH₂—C₆H₄—OCH₃ | H | CH(CH₃)₂ | H | CH₃ | 770 (120 000) | 223–226 |
| 48 | CH(C₂H₅)—C(O)—NH—CH₂—C₆H₄—OCH₃ | H | CH(CH₃)₂ | H | CH₃ | 772 (113 000) | 224–226 |
| 49 | CH₂—C(O)—NH—CH(CH₃)—CH₂—CH₂—C₆H₅ | H | CH(CH₃)₂ | H | CH₃ | 771 (124 000) | 205–207 |
| 50 | CH(C₂H₅)—C(O)—NH—CH(CH₃)—CH₂—CH₂—C₆H₅ | H | CH(CH₃)₂ | H | CH₃ | 769 (111 000) | 224–226 |

TABLE 2-continued

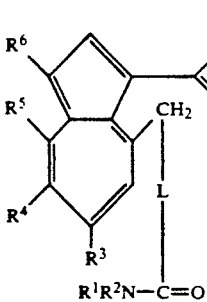

| Example No. | L—C(O)NR¹R² | R³ | R⁴ | R⁵ | R⁶ | λmax (ε) [nm] | mp. [°C] |
|---|---|---|---|---|---|---|---|
| 51 | 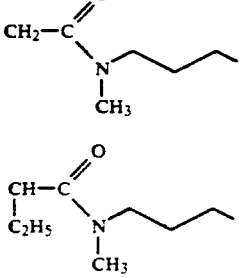 | H | CH(CH$_3$)$_2$ | H | CH$_3$ | 771 (114 000) | 132-134 |
| 52 | 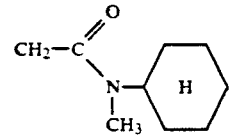 | H | CH(CH$_3$)$_2$ | H | CH$_3$ | 771 (109 000) | 205-207 |
| 53 | 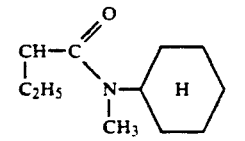 | H | CH(CH$_3$)$_2$ | H | CH$_3$ | 769 (118 000) | 186-188 |
| 54 | | H | CH(CH$_3$)$_2$ | H | CH$_3$ | 771 (120 000) | 152-154 |
| 55 | 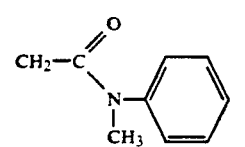 | H | CH(CH$_3$)$_2$ | H | CH$_3$ | 768 (116 000) | 236(dec.) |
| 56 | 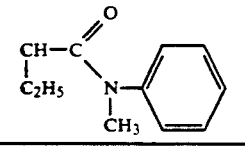 | H | CH(CH$_3$)$_2$ | H | CH$_3$ | 770 (117 000) | 210(dec.) |

EXAMPLE 57

A 5% strength by weight solution of the dye of Example 33 in toluene was applied with a syringe to a polymethyl methacrylate disk rotating at about 2000 rpm, and the remaining solvent was then spun off at 5000 rpm. This produced a homogeneous, highly reflective dye layer which was very readily writable with a semiconductor laser (λ=830 nm). The data can be read back with very good constrast.

EXAMPLE 58

A 3% strength by weight solution of the dye of Example 33 in 1:1 v/v propanol/diacetone alcohol which contained 30% by weight, based on the level of dissolved solids in the solution, of polymethyl methacrylate was applied to a grooved polycarbonate disk by spincoating as described in Example 57. This produced a homogeneous, highly reflective dye layer which is firmly adherent to the substrate, gives a good image of the grooves on the substrate and is very readily writable with a semiconductor laser (λ=830 nm). The written data were stable under hot moist conditions and can be read back with good contrast as often as desired.

EXAMPLE 59

A 2% strength by weight solution of the dye of Example 33 in 1:1 v/v propanol/diacetone alcohol which, based on the level of dissolved solids in the solution, contained 10% by weight of phenolic resin as binder and 5% by weight of 4-octyl-4'-fluorodiphenyldithiolenenickel as stabilizer was applied to a grooved polycarbonate disk by spincoating as described in Example 57. The storage layer obtained was similar in all respects to that of Example 57, but was more stable to UV light.

EXAMPLE 60

A 2% strength by weight solution of the dye of Example 33 in toluene which, based on the level of dissolved solids in the solution, contained 10% by weight of polymethyl methacrylate and 5% by weight of bis-campheratodithiolenenickel was applied to a glass disk by spincoating as described in Example 57. The resulting dye layer was homogeneous and showed a high background reflectivity. It was readily writable with a semiconductor laser ($\lambda = 780$ nm). The written data are stable under the usual test conditions and can be read back as often as desired.

We claim:

1. An amido-containing azulenesquaric acid dye of the formula I

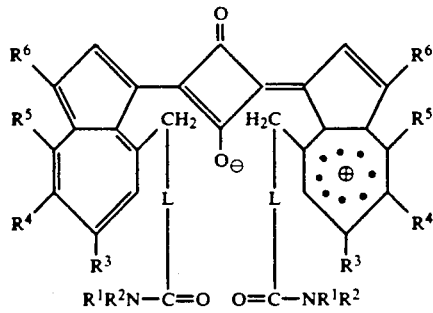

where
  L is $C_1$–$C_{12}$-alkylene which may be substituted by phenyl,
  $R^1$ and $R^2$ are identical or different and each is independently of the other hydrogen, substituted or unsubstituted $C_1$–$C_{20}$-alkyl, $C_5$–$C_7$-cycloalkyl, substituted or unsubstituted phenyl, 2,2,6,6-tetramethylpiperidin-4-yl or cyclohexylaminocarbonyl and
  $R^3$, $R^4$, $R^5$ and $R^6$ are identical or different and each is independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or by cyano,
with the proviso that when $R^6$ is hydrogen the positions of the substituents $CH_2$—L—CO—$NR^1R^2$ and $R^5$ on either or both azulene rings may also be interchanged with each other within an azulene ring.

2. An azulenesquaric acid dye as claimed in claim 1, wherein $R^3$, $R^4$, $R^5$ and $R^6$ are each $C_1$–$C_6$-alkyl or hydrogen.

3. An azulenesquaric acid dye as claimed in claim 1, wherein $R^3$ and $R^5$ are each methyl and $R^4$ and $R^6$ are each hydrogen.

4. An azulenesquaric acid dye as claimed in claim 1, wherein $R^3$ and $R^5$ are each hydrogen, $R^4$ is isopropyl and $R^6$ is methyl.

5. An optical recording medium comprising a base material and a radiation-sensitive thin coating film which contains a dye with or without a binder, wherein the dye has the formula I

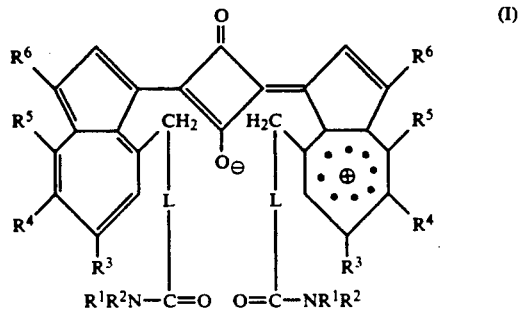

where
  L is $C_1$–$C_{12}$-alkylene which may be substituted by phenyl,
  $R^1$ and $R^2$ are identical or different and each is independently of the other hydrogen, substituted or unsubstituted $C_1$–$C_{20}$-alkyl, $C_5$–$C_7$-cycloalkyl, substituted or unsubstituted phenyl, 2,2,6,6-tetramethylpiperidin-4-yl or cyclohexylaminocarbonyl and
  $R^3$, $R^4$, $R^5$ and $R^6$ are identical or different and each is independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or by cyano,
with the proviso that when $R^6$ is hydrogen the positions of the substituents $CH_2$—L—CO—$NR^1R^2$ and $R^5$ on either or both azulene rings may also be interchanged with each other within an azulene ring.

6. An optical recording medium as claimed in claim 5, wherein $R^3$, $R^4$, $R^5$ and $R^6$ are each $C_1$–$C_6$-alkyl or hydrogen.

7. An optical recording medium as claimed in claim 5, wherein $R^3$ and $R^5$ are each methyl and $R^4$ and $R^6$ are each hydrogen.

8. An optical recording medium as claimed in claim 5, wherein $R^3$ and $R^5$ are each hydrogen, $R^4$ is isopropyl and $R^6$ is methyl.

* * * * *

UNITED STATES PATENT AND TRADEMARK OFFICE
CERTIFICATE OF CORRECTION

PATENT NO. : 5,122,435
DATED : June 16, 1992
INVENTOR(S) : Schmitt et al

It is certified that error appears in the above-identified patent and that said Letters Patent is hereby corrected as shown below:

Column 1, line 51, delete "soluble" and insert --soluble,--;

Column 3, line 67, delete "78" and insert --78--;

Column 7, line 20, after "Pigments" delete "8" and insert --8--.

Signed and Sealed this

Twenty-first Day of September, 1993

Attest:

BRUCE LEHMAN

Attesting Officer

Commissioner of Patents and Trademarks